US012622902B2

(12) United States Patent
Xiao et al.

(10) Patent No.: US 12,622,902 B2
(45) Date of Patent: May 12, 2026

(54) ANTI-ARRHYTHMIC PHARMACEUTICAL COMPOSITION AND PREPARATION METHOD THEREFOR

(71) Applicant: JIANGSU KANION PHARMACEUTICAL CO., LTD., Lianyungang (CN)

(72) Inventors: Wei Xiao, Lianyungang (CN); Hui Zhang, Lianyungang (CN); Qingming Guo, Lianyungang (CN); Zhenzhong Wang, Lianyungang (CN); Xiaolian He, Lianyungang (CN); Xuehong Dong, Lianyungang (CN); Yanqiu Wang, Lianyungang (CN)

(73) Assignee: JIANGSU KANION PHARMACEUTICAL CO., LTD., Lianyungang (CN)

( * ) Notice: Subject to any disclaimer, the term of this patent is extended or adjusted under 35 U.S.C. 154(b) by 739 days.

(21) Appl. No.: 17/912,163

(22) PCT Filed: Mar. 8, 2021

(86) PCT No.: PCT/CN2021/079508
§ 371 (c)(1),
(2) Date: Sep. 16, 2022

(87) PCT Pub. No.: WO2021/196982
PCT Pub. Date: Oct. 7, 2021

(65) Prior Publication Data
US 2023/0135963 A1 May 4, 2023

(30) Foreign Application Priority Data
Mar. 31, 2020 (CN) .......................... 202010246916.0

(51) Int. Cl.
*A61K 31/472* (2006.01)
*A61K 9/20* (2006.01)

(52) U.S. Cl.
CPC .......... *A61K 31/472* (2013.01); *A61K 9/2013* (2013.01); *A61K 9/2018* (2013.01); *A61K 9/2054* (2013.01); *A61K 9/2059* (2013.01); *A61K 9/2095* (2013.01)

(58) Field of Classification Search
CPC .................................................. A61K 31/472
See application file for complete search history.

(56) References Cited

U.S. PATENT DOCUMENTS

| | | | |
|---|---|---|---|
| 10,676,442 B2 * | 6/2020 | Xie ...................... | A61K 31/472 |
| 2017/0216209 A1 | 8/2017 | Schwarz et al. | |
| 2019/0177277 A1 | 6/2019 | Xie et al. | |

FOREIGN PATENT DOCUMENTS

| | | |
|---|---|---|
| CN | 1566098 A | 1/2005 |
| CN | 100422156 C | 10/2008 |
| CN | 104693115 A | 6/2015 |
| CN | 105362245 A | 3/2016 |
| CN | 107778232 A | 3/2018 |
| CN | 107793356 A | 3/2018 |
| EP | 3508478 A1 | 7/2019 |
| JP | 2019526594 A | 9/2019 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS REGISTRYSM) Sep. 2016 2 pages.*
Kawakami, Suppression of pancreatic fistula using drugs— Verification using a rat pancreatic fistula model, Abstracts of the Annual Congress of Japan Surgical Society, 117:2037 (2017).*
Narang, (2015). Excipient Applications in Formulation Design and Drug Delivery.*
International Search Report issued on Jun. 8, 2021 in corresponding International Application No. PCT/CN2021/079508; 4 pages.
Peng, Sixun et al., non-official translation: "Cardiovascular Drug Research: Structural Modification Based on Active Components from Traditional Chinese Medicine", Journal of China Pharmaceutical University, vol. 5, No. 30, Dec. 31, 1999 (Dec. 31, 1999), pp. 396-400, 6 pgs.
Office Action issued on Aug. 20, 2024, in corresponding Japanese Application No. 2022-558472, 6 pages.
Narang et al., "Excipient Applications in Formulation Design and Drug Delivery", Springer, Springer International Publishing, 2015, 700 pages.
Extended Search Report issued on Apr. 8, 2024, in corresponding European Application No. 21781415.1, 22 pages.
Search Report issued on Mar. 31, 2020, in corresponding Chinese Application No. 202010246916.0, 6 pages.
Office Action issued on May 11, 2023, in corresponding Chinese Application No. 202010246916.0, 6 pages.

* cited by examiner

*Primary Examiner* — Nizal S Chandrakumar
(74) *Attorney, Agent, or Firm* — Maier & Maier, PLLC

(57) ABSTRACT

An anti-arrhythmic pharmaceutical composition. The pharmaceutical composition includes: an active ingredient, including 1-(3-methanesulfonamido benzyl)-6-methoxy, 7-benzyloxy-1,2,3,4-tetrahydroisoquinoline or a pharmaceutically acceptable salt thereof; and auxiliary materials, including lactose, microcrystalline cellulose and a pre-gelatinized starch, which account for 30% to 80% of the total weight of the composition. The composition has a good dissolution effect and excellent stability, and can be better applied to clinic.

6 Claims, 2 Drawing Sheets

ANTI-ARRHYTHMIC PHARMACEUTICAL COMPOSITION AND PREPARATION METHOD THEREFOR

TECHNICAL FIELD

The present application belongs to the field of pharmaceutical preparations, and particularly relates to an anti-arrhythmic pharmaceutical composition and a preparation method thereof.

BACKGROUND

Sudden cardiac death (SCD) is one of the main causes of death from cardiovascular diseases. SCD will be caused if regular heart rhythm disappears due to the instability of cardiac electrophysiology. The most serious ones are persistent ventricular tachycardia and ventricular fibrillation.

Patent ZL200710181295.7 discloses 1-(3-methanesulfonamido benzyl)-6-methoxy, 7-benzyloxy-1,2,3,4-tetrahydroisoquinoline (hereinafter referred to as compound A) or a salt thereof. The compound A is known to be a class III anti-arrhythmic drug, can prolong action potential duration, and is effective to ventricular tachycardia and ventricular fibrillation.

SUMMARY

An objective of the present application is to provide an anti-arrhythmic pharmaceutical composition with high stability and rapid dissolution, and a preparation method thereof. Specifically, the pharmaceutical composition provided by the present application includes:

an active ingredient, including 1-(3-methanesulfonamido benzyl)-6-methoxy, 7-benzyloxy-1,2,3,4-tetrahydroisoquinoline or a pharmaceutically acceptable salt thereof; and auxiliary materials, including lactose, microcrystalline cellulose and a pre-gelatinized starch, which account for 30% to 80% of the total weight of the composition.

Further, the lactose, the microcrystalline cellulose and the pre-gelatinized starch account for 40% to 60% of a total weight of the composition.

Preferably, a weight ratio of the lactose to the microcrystalline cellulose to the pre-gelatinized starch is 1:(1.8-2.2):(0.9-1.1). Preferably, the weight ratio is 1:(1.9-2.1):(0.9-1.1). More preferably, the weight ratio is 1:2:1.

Further, the pharmaceutical composition further includes a disintegrating agent, wherein the disintegrating agent is selected from at least one of carboxymethyl starch sodium, croscarmellose sodium, low-substituted hydroxypropyl cellulose and crospovidone.

Further, the disintegrating agent content is 1%-30% of the total weight of the composition, preferably, 2%-20%, more preferably, 2.5%-4%.

Further, the pharmaceutical composition further includes a lubricant, wherein the lubricant is selected from at least one of magnesium stearate, zinc stearate, glyceryl behenate, sodium lauryl sulfate, hydrogenated vegetable oil, superfine silica powder, talcum powder and colloidal silicon dioxide, preferably, at least one of magnesium stearate and colloidal silicon dioxide.

Specifically, the lubricant content is 0.5%-5% of the total weight of the composition, preferably, 0.7%.

Specifically, the pharmaceutical composition may be a granule, tablet or capsule obtained after the active ingredient and the auxiliary materials are subjected to mixing granulation and drying processes.

Further, the active ingredient content is 5%-70% of the total weight of the composition, preferably, 10%-50%, more preferably, 20%-45%. When the pharmaceutical composition is a tablet, the specific weight of the active ingredient content per tablet is 0.1-1000 mg, preferably, 10-500 mg, more preferably, 50-300 mg, further preferably, 100 mg.

Further, the pharmaceutically acceptable salt may be hydrochloride or phosphate.

Further, the pharmaceutical composition further includes an adhesive, wherein the adhesive is selected from at least one of hydroxypropyl methylcellulose, hydroxypropyl cellulose, carboxymethylcellulose sodium, polyvinylpyrrolidone and methylcellulose; and the adhesive content is 0.5%-10% of the total weight of the composition, preferably, 0.9%.

More preferably, the prescription weight ratio of the pharmaceutical composition is as follows:

| Ingredients | Dosage |
|---|---|
| Compound B | 43.6 |
| Lactose | 13.2 |
| Microcrystalline cellulose | 26.4 |
| Pre-gelatinized starch | 13.2 |
| Croscarmellose sodium | 2.9 |

The compound B is phosphate of the compound A.

The present application further provides an application of the pharmaceutical composition as described in any one of the above to anti-arrhythmic therapy.

The present application further provides a method for preparing the pharmaceutical composition as described above. The method includes:

a) mixing and sieving an active ingredient, lactose, microcrystalline cellulose and a pre-gelatinized starch;

b) performing wet granulation;

c) drying; and d) performing granulation arrangement and total mixing.

Specifically, the drying adopts static drying or fluidized drying.

Specifically, the granulation method adopts a high-speed shearing granulation method or a fluidized bed spray granulation method.

Further, when the pharmaceutical composition is selected from a tablet, the method further includes:

weighing 43.6 parts by weight of 1-(3-methanesulfonamido benzyl)-6-methoxy, 7-benzyloxy-1,2,3,4-tetrahydroisoquinoline phosphate, 13.2 parts by weight of lactose, 26.4 parts by weight of microcrystalline cellulose and 13.2 parts by weight of pre-gelatinized starch, mixing the materials uniformly and screening the materials with an 80-mesh sieve;

adding a 75% ethanol solution with 3% hydroxypropyl methylcellulose to prepare a soft material, and screening the material with a 20-mesh sieve for granulation;

performing air-blowing drying at 50° C. by using a hot air circulation oven;

performing granule arrangement by using a 20-mesh sieve;

adding 2.9 parts of croscarmellose sodium and 0.7 part of magnesium stearate into dry granules after granule arrangement; and tableting.

According to the present application, the pharmaceutical composition with the characteristics of rapid dissolution and high stability is finally obtained by screening the types and the dosage ratio of the auxiliary materials. Under the condition of 0.01 mol/L hydrochloric acid medium, the dissolution rate (%) of the active ingredient in the pharmaceutical composition reaches 80% or higher in 30 minutes. Furthermore, the pharmaceutical composition is simple in preparation process and is more suitable for industrialized mass production.

DETAILED DESCRIPTION OF EMBODIMENTS

Figure 1:
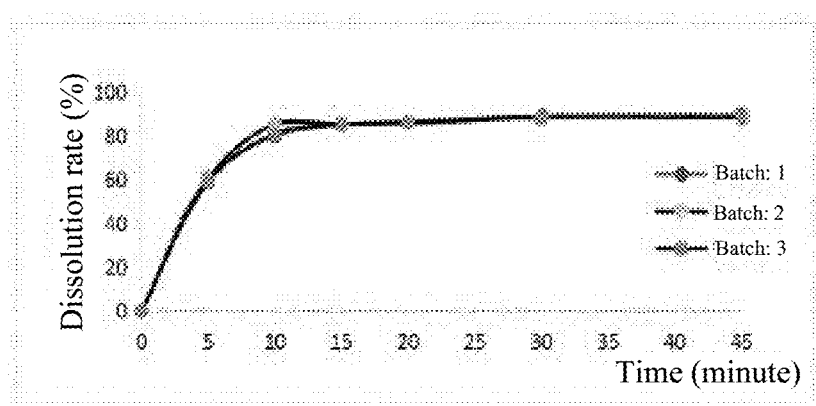
FIG. 1 is a dissolution curve of a pharmaceutical composition according to the present application taking water as a dissolution medium.
Figure 2:
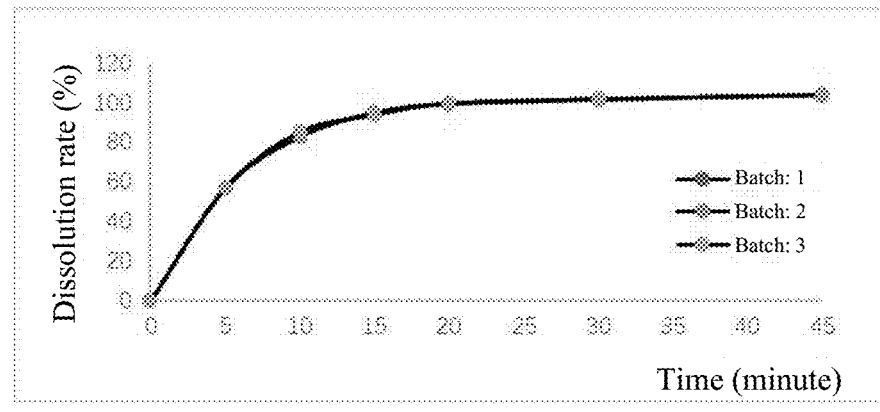
FIG. 2 is a dissolution curve of a pharmaceutical composition according to the present application taking 0.01 mol/L Hydrochloric acid as a dissolution medium.
Figure 3:
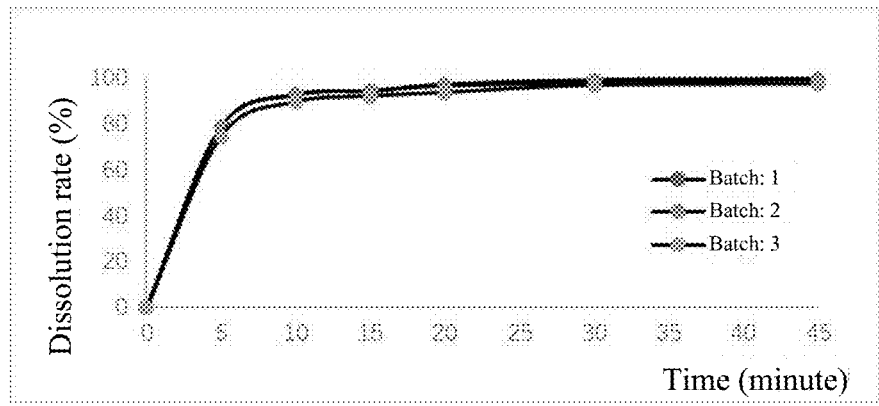
FIG. 3 is a dissolution curve of a pharmaceutical composition according to the present application taking acetic acid buffer salt with the pH of 4.0 as a dissolution medium.
Figure 4:
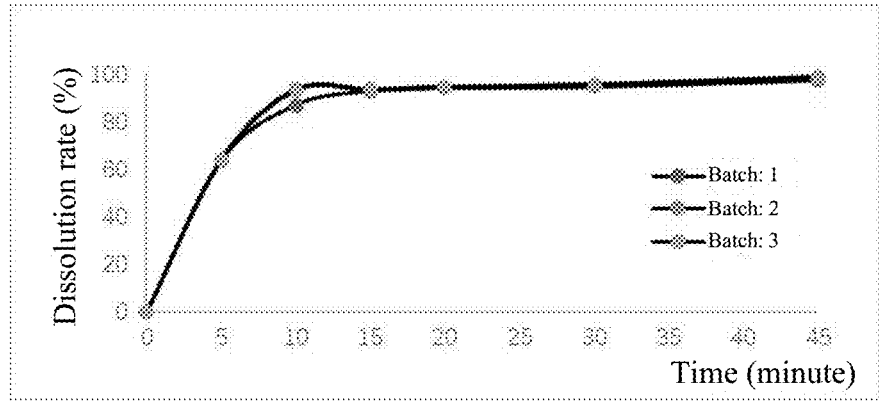
FIG. 4 is a dissolution curve of a pharmaceutical composition according to the present application taking phosphoric acid buffer salt with the pH of 6.8 as a dissolution medium.

The study found that when a pharmaceutical composition was prepared from a compound A and a salt thereof, a drug was decomposed under the condition of moisture and heat, and the pharmaceutical composition absorbs moisture to reduce the dissolution rate of the drug, thereby bringing difficulties to the industrialized mass production of preparations. Accordingly, the present application provides an anti-arrhythmic pharmaceutical composition with high stability and rapid dissolution, and a preparation method thereof.

The present application is further described below by the following embodiments and test examples. The embodiments and test examples are only used to illustrate the objective, but not to limit the scope of the present application.

1. Selecting the Types of Filling Agents

Phosphate of a compound A (hereinafter referred to as compound B), lactose, microcrystalline cellulose and pregelatinized starch were subjected to wet granulation according to a ratio in Table 1, granulation and drying were performed by taking a 3% hydroxypropyl methylcellulose (50 cp) in 60% ethanol solution as an adhesive, then dry granules (the moisture content is less than 3%) were subjected to granule arrangement, the prescription amount of croscarmellose sodium and magnesium stearate were added for mixing, and tableting was performed after uniform mixing according to the standard that each tablet contains 100 mg of compound B. The dissolution rate was measured by using 1000 ml of 0.01 mol/L hydrochloric acid solution according to the second method (slurry method) for determining the dissolution rate in Appendix 0931, Volume IV, Chinese Pharmacopoeia, 2015 (the same below).

TABLE 1

| Names of Raw and Auxiliary Materials | Types of Filling Agents (g) | | | | | | | | |
|---|---|---|---|---|---|---|---|---|---|
| | Prescription 1 | Prescription 2 | Prescription 3 | Prescription 4 | Prescription 5 | Prescription 6 | Prescription 7 | Prescription 8 | Prescription 9 |
| Compound B | 6.1 | 6.1 | 6.1 | 6.1 | 6.1 | 6.1 | 6.1 | 6.1 | 6.1 |
| Lactose | 3.7 | 2.5 | 4.9 | 3.7 | 2.5 | 4.9 | — | — | — |
| Microcrystalline cellulose | 3.7 | 4.9 | 2.5 | — | — | — | 3.7 | 2.5 | 4.9 |
| Pregelatinized starch | — | — | — | 3.7 | 4.9 | 2.5 | 3.7 | 4.9 | 2.5 |
| 60% ethanol solution with 3% hydroxypropyl methylcellulose (ml) | 5.5 | 5.2 | 5.5 | 5.5 | 5.7 | 5.4 | 5.8 | 6.0 | 6.0 |
| Croscarmellose sodium | 0.4 | 0.4 | 0.4 | 0.4 | 0.4 | 0.4 | 0.4 | 0.4 | 0.4 |
| Magnesium stearate | 0.1 | 0.1 | 0.1 | 0.1 | 0.1 | 0.1 | 0.1 | 0.1 | 0.1 |
| Measuring items | | | | | | | | | |
| Granule character | White granule, uniform granularity, hard granule | White granule, uniform granularity, hard granule | White granule, uniform granularity, hard granule | White granule, uniform granularity, hard granule | White granule, uniform granularity, hard granule | White granule, uniform granularity, hard granule | White granule, more fine powder | White granule, more fine powder | White granule, more fine powder |

TABLE 1-continued

| Names of Raw and | Types of Filling Agents (g) | | | | | | | | |
|---|---|---|---|---|---|---|---|---|---|
| Auxiliary Materials | Prescrip-tion 1 | Prescrip-tion 2 | Prescrip-tion 3 | Prescrip-tion 4 | Prescrip-tion 5 | Prescrip-tion 6 | Prescrip-tion 7 | Prescrip-tion 8 | Prescrip-tion 9 |
| Sticking or not | Yes | Yes | Yes | Yes | Yes | Yes | No | No | No |
| Appearance | Coarse surface | Coarse surface | Coarse surface | Coarse surface | Coarse surface | Coarse surface | Bright and clean surface | Bright and clean surface | Bright and clean surface |
| Dissolution phenomenon | Dispersed in 5-10 minutes | Dispersed in 4-10 minutes | Dispersed in 5 minutes | Dispersed in 15 minutes | Dispersed in 15 minutes | Dispersed in 15 minutes | Dispersed in 4-6 minutes | Dispersed in 5 minutes | Dispersed in 3-5 minutes |
| Dissolution rate (%) | 92.09 | 94.13 | 92.34 | 86.12 | 83.13 | 90.33 | 95.40 | 96.49 | 96.28 |

Conclusion: in the prescriptions 1-6, the lactose-microcrystalline granules and the lactose-pre-gelatinized starch granules are excessively hard, and the amount of fine powder in the granules is less, so the appearance of the tablet is affected; the lactose-microcrystalline granules are disintegrated rapidly and have good dissolution rate, but are sticking; and the lactose-pre-gelatinized starch granules are disintegrated slowly, increase the dissolution rate with the increasing of the dosage of the lactose, but are sticking. In the prescriptions 7-9, the microcrystalline-pre-gelatinized starch is disintegrated rapidly and is not sticking, but the amount of fine powder is more. Therefore, the influence of the lactose, the microcrystalline cellulose and the pre-gelatinized starch with different proportions on the formability and dissolution rate of the tablet will be investigated.

2. Selecting the Proportions of Filling Agents

A compound B, lactose, microcrystalline cellulose and pre-gelatinized starch were subjected to wet granulation according to a ratio in Table 2, granulation and drying were performed by taking a 60% ethanol solution with 3% hydroxypropyl methylcellulose (50 cp) as an adhesive, then dry granules (the moisture content is less than 3%) were subjected to granule arrangement, the prescription amount of croscarmellose sodium and magnesium stearate were added for mixing, and tableting was performed after uniform mixing according to the standard that each tablet contains 100 mg of compound A.

TABLE 2

| Investigating the filling agents with different proportions | | | | |
|---|---|---|---|---|
| Names of Raw and Auxiliary Materials | The proportions of the filling agents | | | |
| | Prescription 10 | Prescription 11 | Prescription 12 | Prescription 13 |
| Compound B (g) | 6.1 | 6.1 | 6.1 | 6.1 |
| Lactose (g) | 2.5 | 3.7 | 1.85 | 1.85 |
| Microcrystalline cellulose (g) | 2.5 | 1.85 | 3.7 | 1.85 |
| Pre-gelatinized starch(g) | 2.5 | 1.85 | 1.85 | 3.7 |
| 60% ethanol solution containing 3% hydroxypropyl methylcellulose (50 cp) (ml) | 6.0 | 5.7 | 5.8 | 6.3 |
| Croscarmellose sodium (g) | 0.4 | 0.4 | 0.4 | 0.4 |
| Magnesium stearate (g) | 0.1 | 0.1 | 0.1 | 0.1 |
| Measuring items | | | | |
| Granule character | White granule, uniform granularity, hard granules | White granule, uniform granularity, hard granules | White granule, uniform granularity | White granule, uniform granularity |
| Sticking or not | No | No | No | No |
| Appearance | Coarse surface | Coarse surface | Flat surface | Flat surface |
| Dissolution phenomenon | — | — | Dispersed in 7 minutes | Dispersed in 12 minutes |

Conclusion: in the prescriptions 10 and 11, the lactose content is high, and the prepared granules are hard and have coarse surfaces; in the prescriptions 12 and 13, the granules are uniform and have flat and smooth surfaces; and in the prescription 12, the dissolution rate is high, the large proportion of the pre-gelatinized starch affects the disintegration and dissolution, so the prescription 12 is preferred.

3. Investigating the Types of Disintegrating Agents

A compound B, lactose, microcrystalline cellulose and pre-gelatinized starch were subjected to wet granulation according to a ratio in Table 3, granulation and drying were performed by taking a 75% ethanol solution with 3% hydroxypropyl methylcellulose (50 cp) as an adhesive, then dry granules (the moisture content is less than 3%) were subjected to granule arrangement, croscarmellose sodium/carboxymethyl starch sodium/crospovidone and magnesium stearate in Table 3 were added for mixing, and tableting was performed after uniform mixing according to the standard that each tablet contains 100 mg of compound A.

TABLE 3

| Investigating the disintegrating agents | | | |
|---|---|---|---|
| Names of Raw and | Disintegrating agents | | |
| Auxiliary Materials | Prescription 14 | Prescription 15 | Prescription 16 |
| Compound B (g) | 6.1 | 6.1 | 6.1 |
| Lactose (g) | 1.85 | 1.85 | 1.85 |
| Microcrystalline cellulose (g) | 3.7 | 3.7 | 3.7 |
| Pre-gelatinized starch (g) | 1.85 | 1.85 | 1.85 |
| Magnesium stearate (g) | 0.1 | 0.1 | 0.1 |
| 75% ethanol solution containing 3% hydroxypropyl methylcellulose (50 cp) | 6.0 | 6.0 | 6.0 |
| Croscarmellose sodium (g) | 0.4 | — | — |
| Carboxymethyl starch sodium (g) | — | 0.4 | — |
| Crospovidone (g) | — | — | 0.4 |
| Measuring items | | | |
| Granule character | White granule, uniform granularity | White granule, uniform granularity | White granule, uniform granularity |
| Sticking or not | No | No | No |
| Appearance | Flat and smooth surface | Flat and smooth surface | Flat and smooth surface |
| Dissolution phenomenon | All dispersed in 5 | All dispersed in 12 | All dispersed in 7 |
| Dissolution rate (%) | 95.79 | 90.81 | 94.15 |

Conclusion: according to the granule character, the dissolution phenomenon and the dissolution rate results, the prescription 14 is preferred. The dosage of the filling agents is further screened on the basis of determining the disintegrating agent.

4. Selecting the Dosage of the Filling Agents

A compound B, lactose, microcrystalline cellulose and pre-gelatinized starch were subjected to wet granulation according to a ratio in Table 4, granulation and drying were performed by taking a 75% ethanol solution with 3% hydroxypropyl methylcellulose (50 cp) as an adhesive, then dry granules (the moisture content is less than 3%) were subjected to granule arrangement, croscarmellose sodium and magnesium stearate were added for mixing, and tableting was performed after uniform mixing according to the standard that each tablet contains 100 mg of compound A.

TABLE 4

| Selecting the dosage of the filling agents | | | | |
|---|---|---|---|---|
| Names of Raw and | Filling agents | | | |
| Auxiliary Materials | Prescription 17 | Prescription 18 | Prescription 19 | Prescription 20 |
| Compound B (g) | 6.1 | 6.1 | 6.1 | 6.1 |
| Lactose (g) | 1.85 | 1.85 | 2.05 | 1.15 |
| Microcrystalline cellulose (g) | 3.0 | 4.4 | 3.3 | 4.4 |
| Pre-gelatinized starch(g) | 2.55 | 1.15 | 2.05 | 1.85 |
| Croscarmellose sodium (g) | 0.4 | 0.4 | 0.4 | 0.4 |
| Magnesium stearate (g) | 0.1 | 0.1 | 0.1 | 0.1 |
| 75% ethanol solution containing 3% hydroxypropyl methylcellulose (50 cp) | 6.3 | 6.0 | 6.0 | 6.0 |
| Measuring items | | | | |
| Granule character | White granule, uniform granularity | White granule, uniform granularity | White granule, uniform granularity | White granule, uniform granularity |
| Sticking or not | No | No | No | No |
| Appearance | Flat and smooth surface | The surface is uneven and easy to crack | Flat and smooth surface | The surface is uneven and easy to crack |

TABLE 4-continued

| | Selecting the dosage of the filling agents | | | |
|---|---|---|---|---|
| Names of Raw and | Filling agents | | | |
| Auxiliary Materials | Prescription 17 | Prescription 18 | Prescription 19 | Prescription 20 |
| Dissolution phenomenon | All dispersed in 7 minutes | / | All dispersed in 5 minutes | / |
| Dissolution rate (%) | 89.4 | / | 93.22 | / |

Result: according to the granule character, the dissolution phenomenon and the dissolution rate results, the prescription 14 is preferred.

Two batches of samples (500 tablets in each batch) were prepared respectively according to the prescriptions 14 and 19, and were placed for 30 days under the conditions of high temperature (60° C.), high humidity (75% RH) and illumination (4500 Lx). The result of the influence factor test shows that the dissolution rate, related materials and content in the prescriptions 14 and 19 have no obvious changes under the conditions of high temperature and illumination, but under the condition of high humidity, the appearance of the tablet in the prescription 19 is slightly swelled and the dissolution rate in the prescription 19 is obviously reduced compared with the tablet in the prescription 14.

Conclusion: by the above prescription screening and influence factor test, the prescription 14 has good granule fluidity, tablet appearance, dissolution phenomenon, dissolution rate and stability, so the prescription 14 is determined as the preferred prescription.

According to the preliminarily determined prescription 14, three batches compound B tablets were prepared, with batch number: batch A, batch B and batch C, 3000 tablets in each batch. The quality was studied. After study on the quality of the preparation was completed, three batches of compound B tablets were prepared, with batch number: batch 1, batch 2 and batch 3, 10000 tablets in each batch. The stability was studied.

5. Prescription and Preparation Process

Prescription:

| Ingredients | Dosage |
|---|---|
| Compound B | 43.6 |
| Lactose | 13.2 |
| Microcrystalline cellulose | 26.4 |
| Pre-gelatinized starch | 13.2 |
| Croscarmellose sodium | 2.9 |
| Hydroxypropyl methylcellulose | — |
| Magnesium stearate | 0.7 |
| Total | 100 |

Unit: mass %

Preparation Process:

①  Pretreatment

A compound B, lactose, microcrystalline cellulose and pre-gelatinized starch were mixed uniformly, and the mixture was sieved with a 80-mesh sieve for future use.

②  Granulation

A 75% ethanol solution with 3% hydroxypropyl methylcellulose (50 cp) was added into the pretreated raw and auxiliary materials to prepare a soft material, and the soft material was sieved with a 20-mesh sieve for granulation.

③  Drying

Air-blowing drying was performed at 50° C. by using a hot air circulation oven, and the granules were turned every half hour. The moisture content was measured by a fast moisture determination instrument, drying was finished when the moisture was 2.0%-3.0%, and materials were collected.

④  Granule Arrangement

Granule arrangement was performed by a 20-mesh sieve.

⑤  Total Mixing

Croscarmellose sodium and magnesium stearate were added into dry granules after granule arrangement, and the croscarmellose sodium, the magnesium stearate and the dry granules were mixed in a material bag for 5 minutes.

⑥  Tableting

A 13 mm×6.5 mm elliptic mold tablet press was adopted, tablet weight control: the weight difference should be controlled to be ±5.0%, and the friability should be less than 0.7%.

⑦  Coating

The weight gain of the coating was about 3%.

⑧  Packaging with a White Plastic Bottle

Sealing was performed by an electromagnetic induction aluminum foil sealing machine, with tight aluminum seal and neat appearance.

6. Quality Inspection Data

Three batches of pilot-scale samples (10000 tablets in each batch) were prepared according to the above process. See Table 5 for the test result of the main items.

TABLE 5

| | The test result of the main items of the compound B | | |
|---|---|---|---|
| Inspection items | Batch 1 | Batch 2 | Batch 3 |
| [Character] | This product is a film-coated tablet, which appears white after the coating is removed. | This product is a film-coated tablet, which appears white after the coating is removed. | This product is a film-coated tablet, which appears white after the coating is removed. |
| [Authentication] | Consistent with the relative retention time of the reference solution | Consistent with the relative retention time of the reference solution | Consistent with the relative retention time of the reference solution |

TABLE 5-continued

| The test result of the main items of the compound B | | | |
|---|---|---|---|
| Inspection items | Batch 1 | Batch 2 | Batch 3 |
| | [Inspection] Related substances | | |
| 1-OX | 0.03% | 0.03% | 0.03% |
| Compound 14 | 0.06% | 0.06% | 0.06% |
| Other largest single impurity | 0.08% | 0.08% | 0.08% |
| Total impurity | 0.20% | 0.20% | 0.20% |
| Dissolution rate | 101.7% | 101.5% | 102.1% |
| Weight difference | Conform to specification | Conform to specification | Conform to specification |
| [Content measurement] | 103.3% | 101.0% | 102.4% |

According to the test results of the main items of the three batches of samples, the process of this product is stable.

7. Related Characteristics of the Preparation (1) Dissolution Curve

The dissolution rate was measured according to the second method (slurry method) for determining the dissolution rate in Appendix 0931, Volume IV, Chinese Pharmacopoeia, 2015, 1000 ml of 0.01 mol/L hydrochloric acid solution, acetic acid buffer salt with the pH 4.0, phosphoric acid buffer salt with the pH 6.8 and water were taken as dissolution mediums, and dissolution test was performed at 37.0±0.5° C. and at the propeller speed of 50 rpm. The dissolution curves of four batches of preparation in different dissolution mediums were compared.

The dissolution curve graphs of the four dissolution mediums are attached. By taking the 0.01 mol/L hydrochloric acid solution, acetic acid buffer salt with the pH 4.0, phosphoric acid buffer salt with the pH 6.8 as the dissolution mediums, the dissolution rate of this product is over 85% in 15 minutes; and by taking the water as the dissolution medium, the dissolution rate is close to 85% in 15 minutes.

(2) Related Substances

The test results of three batches of related substances are shown in Table 6.

TABLE 6

| The measured results of three batches of compounds B | | | |
|---|---|---|---|
| | | Batch number | |
| Related substances (%) | Batch 1 | Batch 2 | Batch 3 |
| 1-OX | 0.03% | 0.03% | 0.03% |
| Largest single impurity | 0.06% | 0.06% | 0.06% |
| Other largest single impurity | 0.08% | 0.08% | 0.08% |
| Total impurity | 0.20% | 0.20% | 0.20% |

The properties of the raw materials of this product are stable, the raw and auxiliary materials in the preparation are good in compatibility, single impurity does not exceed 0.1%, and the related substances of three batches of preparations all conform to the specification.

(3) Stability

① Influence Factor Test

Batch number: batch 1; batch: 10000 tablets; specification: 0.1 g; package: high-density polyethylene bottle for oral solid drugs

TABLE 7

| The investigation results of the influence factors | | | | | | | | |
|---|---|---|---|---|---|---|---|---|
| Investigation target | Time (day) | Character | 1-OX (%) | Largest single impurity (%) | Other largest single impurity (%) | Total impurity (%) | Dissolution rate (%) | Content (%) |
| Quality standard | | After the coating was removed, it should be white or off-white | ≤0.2% | ≤0.2% | ≤0.2% | ≤1.5% | ≥80.0% | It should be 90.0%-110.0% of the labeled amount |
| 60° C. high-temperature test | 0 | Conformity | 0.03 | 0.06 | 0.08 | 0.20 | 101.7 | 103.3 |
| | 5 | Conformity | 0.03 | 0.08 | 0.09 | 0.22 | 98.8 | 102.8 |
| | 10 | Conformity | 0.03 | 0.07 | 0.10 | 0.22 | 102.0 | 102.6 |
| | 30 | Conformity | 0.02 | 0.07 | 0.11 | 0.24 | 94.0 | 103.1 |
| 4500 Lx strong illumination test | 0 | Conformity | 0.03 | 0.06 | 0.08 | 0.20 | 101.7 | 103.3 |
| | 5 | Conformity | 0.02 | 0.07 | 0.09 | 0.21 | 99.7 | 103.2 |
| | 10 | Conformity | 0.03 | 0.07 | 0.09 | 0.22 | 102.7 | 103.3 |
| | 30 | Conformity | 0.02 | 0.07 | 0.10 | 0.22 | 96.4 | 102.7 |
| 90% RH high-humidity test | 0 | Conformity | 0.03 | 0.06 | 0.08 | 0.20 | 101.7 | 103.3 |
| | 5 | Conformity | 0.03 | 0.08 | 0.09 | 0.23 | 99.9 | 103.5 |
| | 10 | Conformity | 0.03 | 0.07 | 0.10 | 0.22 | 101.9 | 102.4 |
| | 30 | Conformity | 0.03 | 0.07 | 0.10 | 0.23 | 95.3 | 102.9 |

13 14

Conclusion: the test results of the compound B tablets under the conditions of high temperature, high humidity and illumination for 0, 5, 10 and 30 days: the sample character, the related substances, the dissolution rate and the content have no significant changes compared with those in 0 day.

② Acceleration Test

Batch number: batch 1; batch: 10000 tablets; specification: 0.1 g; package: high-density polyethylene bottle for oral solid drugs; and investigation conditions: 40° C.±2° C. and RH75%±5%.

TABLE 8

Acceleration stability investigation-batch 1

| Investigation items | Limit requirement | Time (month) | | | | |
|---|---|---|---|---|---|---|
| | | 0 | 1 | 2 | 3 | 6 |
| Character | After the coating was removed, it should be white or off-white | After the coating was removed, it should be white | After the coating was removed, it should be white | After the coating was removed, it should be white | After the coating was removed, it should be white | After the coating was removed, it should be white |
| Related substances (%) | The debenzylated impurity should be less than or equal to 0.2% | Not Detected | Not Detected | Not Detected | Not Detected | Not Detected |
| | 1-OX should be less than or equal to 0.2% | 0.03 | 0.03 | 0.03 | 0.03 | 0.03 |
| | The compound 14 should be less than or equal to 0.2% | 0.06 | 0.06 | 0.06 | 0.06 | 0.05 |
| | Other largest single impurity should be less than or equal to 0.2% | 0.08 | 0.09 | 0.09 | 0.09 | 0.06 |
| | Total impurity should be less than or equal to 1.0% | 0.20 | 0.21 | 0.20 | 0.22 | 0.15 |
| Dissolution rate (%) | should be greater than or equal to 80% | 101.7 | 103.5 | 101.2 | 101.8 | 100.1 |
| Content (%) | It should be 90.0%-110.0% of the labeled amount | 103.3 | 102.3 | 102.2 | 101.8 | 102.1 |

35

Batch number: batch 2; batch: 10000 tablets; specification: 0.1 g; package: high-density polyethylene bottle for oral solid drugs; and investigation conditions: 40° C.±2° C. and RH75%±5%

TABLE 9

Acceleration stability investigation-batch 2

| Investigation items | Limit requirement | Time (month) | | | | |
|---|---|---|---|---|---|---|
| | | 0 | 1 | 2 | 3 | 6 |
| Character | After the coating was removed, it should be white or off-white | After the coating was removed, it should be white | After the coating was removed, it should be white | After the coating was removed, it should be white | After the coating was removed, it should be white | After the coating was removed, it should be white |
| Related substances (%) | The debenzylated impurity should be less than or equal to 0.2% | Not Detected | Not Detected | Not Detected | Not Detected | Not Detected |
| | 1-OX should be less than or equal to 0.2% | 0.03 | 0.03 | 0.03 | 0.03 | 0.03 |
| | The largest single impurity should be less than or equal to 0.2% | 0.06 | 0.06 | 0.06 | 0.06 | 0.06 |
| | Other largest single impurity should be less than or equal to 0.2% | 0.08 | 0.08 | 0.08 | 0.10 | 0.08 |
| | Total impurity should be less than or equal to 1.0% | 0.20 | 0.20 | 0.20 | 0.22 | 0.17 |

TABLE 9-continued

| Investigation | | Time (month) | | | | |
|---|---|---|---|---|---|---|
| items | Limit requirement | 0 | 1 | 2 | 3 | 6 |
| | | | | | | |
| Dissolution rate (%) | should be greater than or equal to 80% | 101.5 | 102.2 | 98.0 | 102.2 | 100.1 |
| Content (%) | It should be 90.0%-110.0% of the labeled amount | 101.0 | 100.4 | 100.0 | 100.3 | 100.6 |

*Acceleration stability investigation-batch 2*

Batch number: batch 3; batch: 10000 tablets; specification: 0.1 g; package: high-density polyethylene bottle for oral solid drugs; and investigation conditions: 40° C.±2° C. and RH75%±5%

TABLE 10

*Acceleration stability investigation-batch 3*

| Investigation | | Time (month) | | | | |
|---|---|---|---|---|---|---|
| items | Limit requirement | 0 | 1 | 2 | 3 | 6 |
| | | | | | | |
| Character | After the coating was removed, it should be white or off-white | After the coating was removed, it should be white | After the coating was removed, it should be white | After the coating was removed, it should be white | After the coating was removed, it should be white | After the coating was removed, it should be white |
| Related substances (%) | The debenzylated impurity should be less than or equal to 0.2% | Not Detected | Not Detected | Not Detected | Not Detected | Not Detected |
| | 1-OX should be less than or equal to 0.2% | 0.03 | 0.03 | 0.03 | 0.03 | 0.03 |
| | The largest single impurity should be less than or equal to 0.2% | 0.06 | 0.06 | 0.06 | 0.06 | 0.06 |
| | Other largest single impurity should be less than or equal to 0.2% | 0.08 | 0.09 | 0.09 | 0.09 | 0.08 |
| | Total impurity should be less than or equal to 1.0% | 0.20 | 0.20 | 0.21 | 0.21 | 0.17 |
| Dissolution rate (%) | should be greater than or equal to 80% | 102.1 | 102.7 | 100.1 | 103.9 | 99.6 |
| Content (%) | It should be 90.0%-110.0% of the labeled amount | 102.4 | 101.6 | 101.4 | 101.2 | 101.8 |

Conclusion: the results of the accelerated stability test of three batches of samples of the compound B tablets for 6 months show that: compared with those in 0 month, the character, related substances, dissolution rate and content of this product have not significant changes in each test indexes, indicating that the accelerated stability test results of this product are good.

③ Long-Term Test

Batch number: batch 1; batch: 10000 tablets; specification: 0.1 g; package: high-density polyethylene bottle for oral solid drugs; and investigation conditions: 30° C.±2° C. and RH65%±5%

TABLE 11

*Long-term stability investigation-batch 1*

| Investigation | | Time (month) | | | | |
|---|---|---|---|---|---|---|
| items | Limit requirement | 0 | 3 | 6 | 9 | 12 |
| | | | | | | |
| Character | After the coating was removed, it should be white or off-white | After the coating was removed, it should be white | After the coating was removed, it should be white | After the coating was removed, it should be white | After the coating was removed, it should be white | After the coating was removed, it should be white |

TABLE 11-continued

| Investigation | | Time (month) | | | | |
|---|---|---|---|---|---|---|
| items | Limit requirement | 0 | 3 | 6 | 9 | 12 |
| Related substances (%) | The debenzylated impurity should be less than or equal to 0.2% | Not Detected | Not Detected | Not Detected | Not Detected | Not Detected |
| | 1-OX should be less than or equal to 0.2% | 0.03 | 0.04 | 0.03 | 0.02 | 0.04 |
| | The largest single impurity should be less than or equal to 0.2% | 0.06 | 0.06 | 0.07 | 0.06 | 0.06 |
| | Other largest single impurity should be less than or equal to 0.2% | 0.08 | 0.10 | 0.09 | 0.07 | 0.09 |
| | Total impurity should be less than or equal to 1.0% | 0.20 | 0.23 | 0.20 | 0.16 | 0.20 |
| Dissolution rate (%) | should be greater than or equal to 80% | 101.7 | 100.2 | 100.2 | 101.7 | 98.1 |
| Content (%) | It should be 90.0%-110.0% of the labeled amount | 103.3 | 101.8 | 102.1 | 101.6 | 101.4 |

Long-term stability investigation-batch 1

Batch number: batch 2; batch: 10000 tablets; specification: 0.1 g; package: high-density polyethylene bottle for oral solid drugs; and investigation conditions: 30° C.±2° C. and RH65%±5%

TABLE 12

| Investigation | | Time (month) | | | | |
|---|---|---|---|---|---|---|
| items | Limit requirement | 0 | 3 | 6 | 9 | 12 |
| Character | After the coating was removed, it should be white or off-white | After the coating was removed, it should be white | After the coating was removed, it should be white | After the coating was removed, it should be white | After the coating was removed, it should be white | After the coating was removed, it should be white |
| Related substances (%) | The debenzylated impurity should be less than or equal to 0.2% | Not Detected | Not Detected | Not Detected | Not Detected | Not Detected |
| | 1-OX should be less than or equal to 0.2% | 0.03 | 0.03 | 0.04 | 0.03 | 0.04 |
| | The largest single impurity should be less than or equal to 0.2% | 0.06 | 0.06 | 0.06 | 0.06 | 0.09 |
| | Other largest single impurity should be less than or equal to 0.2% | 0.08 | 0.09 | 0.08 | 0.06 | 0.09 |
| | Total impurity should be less than or equal to 1.0% | 0.20 | 0.22 | 0.18 | 0.16 | 0.32 |
| Dissolution rate (%) | should be greater than or equal to 80% | 101.5 | 101.7 | 100.1 | 101.9 | 101.7 |
| Content (%) | It should be 90.0%-110.0% of the labeled amount | 101.0 | 100.2 | 100.5 | 100.1 | 100.1 |

Long-term stability investigation-batch 2

Batch number: batch 3; batch: 10000 tablets; specification: 0.1 g; package: high-density polyethylene bottle for oral solid drugs; and investigation conditions: 30° C.±2° C. and RH65%±5%

TABLE 13

| | | Long-term stability investigation-batch 3 | | | | |
|---|---|---|---|---|---|---|
| Investigation | | Time (month) | | | | |
| items | Limit requirement | 0 | 3 | 6 | 9 | 12 |
| Character | After the coating was removed, it should be white or off-white | After the coating was removed, it should be white | After the coating was removed, it should be white | After the coating was removed, it should be white | After the coating was removed, it should be white | After the coating was removed, it should be white |
| Related substances (%) | The debenzylated impurity should be less than or equal to 0.2% | Not Detected | Not Detected | Not Detected | Not Detected | Not Detected |
| | 1-OX should be less than or equal to 0.2% | 0.03 | 0.03 | 0.04 | 0.03 | 0.04 |
| | The largest single impurity should be less than or equal to 0.2% | 0.06 | 0.06 | 0.07 | 0.05 | 0.07 |
| | Other largest single impurity should be less than or equal to 0.2% | 0.08 | 0.09 | 0.08 | 0.06 | 0.08 |
| | Total impurity should be less than or equal to 1.0% | 0.20 | 0.21 | 0.19 | 0.15 | 0.20 |
| Dissolution rate (%) | should be greater than or equal to 80% | 102.1 | 101.3 | 99.8 | 101.1 | 102.1 |
| Content (%) | It should be 90.0%-110.0% of the labeled amount | 102.4 | 101.6 | 101.3 | 101.3 | 101.5 |

Conclusion: the results of the long-term stability test of three batches of samples of the compound B tablets for 12 months show that: compared with those in 0 month, the character, related substances, dissolution rate and content of this product have not significant changes in each test indexes, indicating that the long-term stability test results of this product are good.

Conclusion: the accelerated 6-month and long-term 12-month stability tests of three batches of samples of the compound B tablets of the present application show that: this product is sealed and stored under the proposed packaging conditions (high-density polyethylene bottle for oral solid drugs), which can ensure the good stability of the samples.

It should be noted that those skilled in the art may learn from the contents of the specification to appropriately improve process parameters, and all the similar substitutions and modifications are obvious to those skilled in the art and should be considered to be included in the present application.

What is claimed is:

1. A pharmaceutical composition for treating arrhythmia, comprising:
43.6 parts by weight of 1-(3-methanesulfonamido benzyl)-6-methoxy, 7-benzyloxy-1,2,3,4-tetrahydroisoquinoline phosphate, 13.2 parts by weight of lactose, 26.4 parts by weight of microcrystalline cellulose, 13.2 parts by weight of pre-gelatinized starch, 2.9 parts, of croscarmellose sodium and 0.7 parts of magnesium stearate.

2. The pharmaceutical composition according to claim 1, wherein the pharmaceutical composition is a granule, tablet or capsule.

3. The pharmaceutical composition according to claim 1, further comprising an adhesive, wherein:

the adhesive is selected from at least one of hydroxypropyl methylcellulose, hydroxypropyl cellulose, carboxymethylcellulose sodium, polyvinylpyrrolidone and methylcellulose; and the adhesive content is 0.5%-10% of the total weight of the composition.

4. A method for preparing the pharmaceutical composition according to claim 1, comprising:
a) mixing and sieving an active ingredient, lactose, microcrystalline cellulose and a pre-gelatinized starch;
b) performing wet granulation;
c) performing dynamic drying; and
d) performing granule arrangement and total mixing.

5. The method according to claim 4, wherein when the pharmaceutical composition is selected from a tablet, the method comprises:

weighing 43.6 parts by weight of 1-(3-methanesulfonamido benzyl)-6-methoxy, 7-benzyloxy-1,2,3,4-tetrahydroisoquinoline phosphate, 13.2 parts by weight of lactose, 26.4 parts by weight of microcrystalline cellulose and 13.2 parts by weight of pre-gelatinized starch, mixing the materials uniformly and sieving the materials with a 80-mesh sieve;

adding a 75% ethanol solution with 3% hydroxypropyl methylcellulose to prepare a soft material, and sieving the material with a 20-mesh sieve for granulation;

performing air-blowing drying at 50° C. by using a hot air circulation oven;

performing granule arrangement by using a 20-mesh sieve;

adding 2.9 parts of croscarmellose sodium and 0.7 parts of magnesium stearate into dry granules after granule arrangement; and tableting.

6. The pharmaceutical composition according to claim 3, wherein the adhesive content is 1.25% of the total weight of the composition.

* * * * *